DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JULY 6, 1976

948 O.G. 6

T948,005

CATALYTIC VAPOR PHASE OXIDATION OF ISOBUTYLENE

David C. Lini, 705 Pine Ridge Road, Springfield, Pa. 19063, and John J. McCoy, 825 Rhoads Drive, Media, Pa. 19064

Continuation of abandoned application Ser. No. 370,095, June 11, 1973. This aplication June 30, 1975, Ser. No. 591,543

Int. Cl. C07c *45/04*
U.S. Cl. 260—604 R
No Drawing. 11 Pages of Specification

Isobutylene is oxidized to methacrolein in the vapor phase with molecular oxygen at temperatures in the range of from 970° F. to 1150° F. in the presence of a bismuth molybdate or bismuth phosphomolybdate catalyst in particulate form admixed with masses of a metal or metal alloy having a melting point ranging from above the reaction temperature employed up to about 250° F. above the reaction temperature to aid in the dissipation of the exothermic heat of reaction and thereby improve the selectivity of the reaction for the production of methacrolein.